United States Patent [19]
Perez

[11] Patent Number: 5,543,146
[45] Date of Patent: Aug. 6, 1996

[54] DIETARY SUPPLEMENT FOR ALLEVIATING THE SYMPTOMS ASSOCIATED WITH ENLARGEMENT OF THE PROSTATE GLAND

[75] Inventor: Carlos Perez, Coral Gables, Fla.

[73] Assignee: Prostahelp, Inc., Coral Gables, Fla.

[21] Appl. No.: 526,992

[22] Filed: Sep. 12, 1995

Related U.S. Application Data

[63] Continuation-in-part of Ser. No. 375,608, Jan. 20, 1995, abandoned.

[51] Int. Cl.$^6$ .......................... A61K 35/78; A61K 9/20; A61K 33/32
[52] U.S. Cl. ............ 424/195.1; 424/464; 424/641; 424/643; 514/458
[58] Field of Search ................. 424/195.1, 464, 424/641, 643; 514/458

[56] References Cited

U.S. PATENT DOCUMENTS

| | | | |
|---|---|---|---|
| 3,856,946 | 12/1974 | Debat | 424/195.1 |
| 4,011,313 | 3/1977 | Thompson | 514/153 |
| 4,258,037 | 3/1981 | Juvin | 424/195.1 |
| 5,340,803 | 8/1994 | Rubin | 514/25 |
| 5,382,430 | 1/1995 | Soma et al. | 424/195.1 |
| 5,405,613 | 4/1995 | Rowland | 424/439 |
| 5,411,748 | 5/1995 | Song | 424/559 |
| 5,476,842 | 12/1995 | Rubin | 514/25 |

*Primary Examiner*—John W. Rollins
*Attorney, Agent, or Firm*—Robert M. Downey, P.A.

[57] ABSTRACT

A composition for a dietary supplement includes: 12.5 to 25% pumpkin seeds by weight; 1,875 to 18.75% extract of *Serenoa repens* by weight; 6.25 to 12.5% *Pygeum africanum* by weight; 3.125 to 6.25% zinc glycinate by weight; 3.125 to 9.375% magnesium by weight; and 9,375 to 18.75% vitamin E acetate by weight. The composition may further include Di-Tab, Syloid and magnesium stearate as excipients.

3 Claims, No Drawings

DIETARY SUPPLEMENT FOR ALLEVIATING THE SYMPTOMS ASSOCIATED WITH ENLARGEMENT OF THE PROSTATE GLAND

BACKGROUND OF THE INVENTION

This application is a continuation-in-part application of patent application Ser. No. 08/375,608 filed on Jan. 20, 1995 now abandoned.

FIELD OF THE INVENTION

The present invention relates to a dietary supplement, and more particularly, to a dietary supplement for alleviating the symptoms associated with enlargement of the prostate gland.

DESCRIPTION OF THE RELATED ART

It is well known that many disorders are the result of dietary deficiencies wherein the body is starved of certain vitamins, minerals and other natural elements. Other disorders are simply the result of aging. Disorders due to aging may result if the body produces too much or too little of certain enzymes or hormones, thereby affecting the body's metabolism. Some disorders can be treated or corrected by supplementing missing natural elements which are ordinarily not found in the average diet. Through the use of a daily supplement, supplying these missing vitamins and natural elements, the symptoms of various disorders may improve or disappear entirely.

In men, the prostate gland is the source of several common disorders including prostatitis and benign prostatic hypertrophy, wherein the prostrate gland becomes inflamed or enlarged. Benign prostatic hypertrophy (BPH) occurs naturally in most males over 50 years of age. At this age, the male body begins to transform testosterone (male sex hormone) into dihydroxytestosterone (DHT), at higher levels, within the prostrate. This is primarily due to higher levels of the enzyme reductase which causes the conversion of testosterone to DHT. DHT has a tendency to bind to prostatic receptor cells which ultimately results in prostate enlargement. It is usually a benign condition and, thus, in some cases there is no need for surgery. However, enlargement of the prostate gland can cause many uncomfortable and annoying symptoms including:

difficulty in starting to urinate;

increased urge to urinate;

a weak or interrupted stream when urinating;

a feeling that you can not empty your bladder completely;

a feeling of delay when you start to urinate;

a need to urinate often, especially at night; and frequent or continuous lower back pain.

Nearly 400,000 prostate surgical procedures are performed annually to treat enlarge prostates. Numerous laboratories are conducting research in an attempt to find a cure for BPH (benign prostatic hypertrophy). In 1992, several new drugs were introduced to the market which resulted in reductions of approximately 60%–70% of nicturia, 50% in diuria frequency, and 40% in post mictional residue. However, some doctors have reported that as many 15% of patients have complained of impotency after taking these drugs. Additionally, there are side effects which are noted by the FDA, as reported in the Jan., 1995 issue of U.S. News and World Report.

There are natural elements which have known benefits in treating enlargement of the prostate gland and prostatitis. Specifically, it is widely accepted in the field of medicine that zinc has positive effects in reducing an enlarged prostate (see "What Every Man Should Know About His Prostate," Monroe E. Greenberger, M. D. and Mary Ellen Siegel MSW, pages 96–105). However, studies have indicated that when zinc is administered orally, it is difficult to reach the prostatic tissue. Therefore, the prostate does not reap the full benefits of the zinc.

Other studies have shown that *Pygeum africanum* extract has definite effects in reducing the size of the prostate (please refer to "Medical Treatment of Benign Prostatic Hypertrophy with the *Pygeum africanum* Extract," R. M. Scarpa, R. Migliari, G. Campus, A. DeLisa, M. Sorgia, M. Usai, E. Usai, Urology Clinic of the University of Cagliari).

Further, extensive studies carried out in Europe have established that saw palmetto (*Serenoa repens*) effectively reduces the size of the enlarged prostate and restores function. The saw palmetto berry contains an oil composed of sterols and various saturated and unsaturated fatty acids. In Europe, and now in the United States, the purified fat soluble extract from the saw palmetto berry is used medicinally.

Another natural product known to have beneficial effects on the enlarged prostate is pumpkin seeds. While there are no significant medical studies, pumpkin seeds have been used as folk remedy for centuries. In fact, it is believed that Hungarian gypsies, Ukrainians and Transylvanian's do not suffer from BPH because these cultures eat pumpkin seeds from childhood as part of their daily diet.

Presently, in the United States, most patients suffering from benign prostatic hypertrophy and prostatitis are treated with drugs such as Hytrin® (Terazosin-HCI), manufactured by Abbott Laboratories, Proscar®, manufactured by Merck and Company, Inc., and Flutamide®. While these drugs have beneficial effects in treating BPH, they have known side effects, including impotency in men. More specifically, Proscar® is known to be transmitted to females through semen during sexual intercourse, presenting a significant health risk to women who are or could become pregnant. Further, the FDA has reported that Hytrin® may cause Prioprism, resulting in persistent, painful erections which can permanently damage the penis. The side effects of Flutamide® include painful swelling of the man's breasts as well as nausea, vomiting and diarrhea.

SUMMARY OF THE INVENTION

The present invention is directed to a dietary supplement for alleviating the symptoms associated with enlargement of the prostate gland and inflammation of the prostate gland and comprising pumpkin seeds, zinc glycinate, extract of *serenoa repens, Pygeum africanum,* magnesium and Vitamin E acetate. While some of these elements have known benefits to the prostate gland, as stated above, it has been found that when combined in accordance with determined proportionate ranges, the combined ingredients have synergistic effects on reduction of the size of the prostate gland, thereby providing more immediate and dramatic relief to those suffering from the symptoms associated with BPH and prostatitis, without the adverse side effects as experienced with the above mentioned drugs. The efficacy of the composition was determined by monitoring various parameters including serum prostate-specific antigen (PSA) concentrations of patients over 90 day periods, nicturia, diuria and urine flow rate. These results were compared to known results in past studies using only one element, or a sub-combination of elements of the composition.

The fundamental elements of the composition of the present invention include 400 to 800 mg of pumpkin seeds, 100 to 200 mg of zinc glycinate, 60 to 600 mg extract of *Serenoa repens* (saw palmetto extract), 200 to 400 mg of *Pygeum africanum*, 100 to 300 mg magnesium, and 300 to 600 I. U. Vitamin E acetate.

In accordance with the composition of the present invention, it is a primary object to provide a dietary supplement having beneficial effects in treating prostate gland disorders.

It is a further object of the present invention to provide a dietary supplement comprised of natural ingredients including pumpkin seeds, zinc glycinate, extract of *Serenoa repens, pygeum africanum*, magnesium and Vitamin E acetate, which, in combination, yield synergistic effects in treating the symptoms associated with BPH and prostatitis.

It is still a further object of the present invention to provide a dietary supplement comprised of all natural ingredient for treating the symptoms associated with BPH and prostatitis and which has no adverse side effects.

The fundamental elements of the composition include pumpkin seeds in an amount of between 12.5% to 25% by weight of the composition, extract of *Serenoa repens* (saw palmetto extract) in an amount of between 1,875% to 18.75% by weight of the composition and *Pygeum africanum* in an amount of between 6.25% to 12.55% by weight of the composition. The composition further includes zinc glycinate in an amount of between 3,125% to 6.25% by weight, magnesium in an amount of between 3.125% to 9.375% by weight, and Vitamin E acetate in an amount of between 9.375% to 18.75% by weight of the composition.

The composition preferably includes 25% to 35% by weight Di-Tab, 0.8% to 1.2% by weight Syloid and 0.8% to 1.2% by weight magnesium stearate as excipients.

The composition is preferably provided in the form of tablets or capsules. To do this, the ingredients are first weighed in order to obtain the desired percentage by weight of each of the ingredients to be mixed. Both *Serenoa repens* and *Pygeum africanum* are readily available in liquid or power form. Liquid is preferred for use in capsules while powder is used for tablets. The ingredients are homogenized directly or in the presence of water by placing the ingredients in a ribbon blender, wherein the ingredients are mixed at medium to high speeds for 20 minutes at a temperature of between 70 to 80 degrees Fahrenheit. The mixture is then placed in dies in a compression machine to mold the mixture into tablets. The compression machine generates a compression of 7 tons, sufficiently compacting the mixture into a uniform, integral tablet. After compression, the tablets are coated with a fine coat of pharmaceutical glaze in order to eliminate dust, prevent the tablets from breaking apart and enhance their appearance. The coated tablets are then placed in bottles (preferably 60 tablets to a bottle) and labeled for shipping and distribution.

EXAMPLES OF THE COMPOSITION

| Example 1 | W % |
| --- | --- |
| Pumpkin seeds | 18.75 |
| Zinc glycinate | 3.125 |
| Magnesium | 6.25 |
| Vitamin E acetate | 9.375 |
| Extract of *serenoa repens* (saw palmetto extract) | 15.625 |
| *Pygeum africanum* | 9.375 |

| Example 1 | W % |
| --- | --- |
| Excipients, including: Di-Tab Syloid Magnesium stearate | 37.5 |

The recommended dosage for the average adult male is 6 tablets a day which will provide the following amounts of each of the active ingredients of example 1:

| Pumpkin seeds | 600 mg |
| --- | --- |
| Zinc glycinate | 100 mg |
| Magnesium | 200 mg |
| Vitamin E | 300 IU |
| Saw palmetto extract | 500 mg |
| *Pygeum africanum* | 300 mg |

| Example 2 | W % |
| --- | --- |
| Pumpkin seeds | 12.5 |
| Zinc glycinate | 6.25 |
| Magnesium | 3.125 |
| Vitamin E acetate | 18.75 |
| Saw palmetto extract | 18.75 |
| *Pygeum africanum* | 6.25 |
| Excipients, including: Di-Tab Syloid Magnesium stearate | 34.375 |

| Example 3 | W % |
| --- | --- |
| Pumpkin seeds | 25.0 |
| Saw palmetto extract | 1.875 |
| *Pygeum africanum* | 12.5 |
| Zinc glycinate | 6.25 |
| Excipients | 45.625 |

Each of the three examples of the composition were tested with patients suffering from BPH. The efficacy of each of the three examples was determined by measuring various parameters including prostate-specific antigen concentration (PSA), nicturia, diuria, and maximum urinary flow rate. The results of each of these parameters were compared with known results in the identical parameters for patients treated with individual elements or sub-combinations of the elements of the composition. The overall results ranged between 5 to 8 times greater efficacy of the above three examples compared to the known results of studies using the individual elements or sub-combinations. The determined efficacy of the composition of the above examples reveals that there is a synergistic effect when combining the elements of the composition within the established range of proportions.

While the composition of the present invention has been set forth in what is believed to be preferred embodiments, it is recognized that departures may be made within the spirit and scope of the following claims which, therefore, should not be limited except within the doctrine of equivalents.

Now that the invention has been described, What is claimed is:

1. A dietary supplement for alleviating the symptoms associated with enlargement of the prostate gland, comprising the following ingredients:

pumpkin seeds in an amount of between 12.50 to 25% by weight of the composition;

extract of *Serenoa repens* in an amount of between 1.875 to 18.75% by weight of the composition;

*Pygeum africanum* in an amount of between 6.25 to 12.5% by weight of the composition;

zinc glycinate in an amount of between 3.125 to 6.25% by weight of the composition; and excipients, wherein the amount of ingredients in the dietary supplement totals 100%.

2. The dietary supplement as set forth in claim 1 which further comprises the following ingredients:

magnesium in an amount of between 3.125 to 9.375% by weight of the composition; and vitamin E acetate in an amount of between 9.375 to 18.75% by weight of the composition, wherein the amount of ingredients in the dietary supplement totals 100%.

3. A dietary supplement for alleviating the symptoms associated with enlargement of the prostate gland, comprising the following ingredients:

pumpkin seeds in an amount of between 12.5 to 25% by weight of the composition;

zinc glycinate in an amount of between 3.125 to 6.25% by weight of the composition;

magnesium in an amount of between 3.125 to 9.375% by weight of the composition;

vitamin E acetate in an amount of between 9.375 to 18.75% by weight of the composition;

extract of *Serenoa repens* in an amount of between 1.875 to 18.75% by weight of the composition; and

*Pygeum africanum* in an amount of between 6.25 to 12.5% by weight of the composition.

* * * * *